(12) United States Patent
Cohen et al.

(10) Patent No.: US 11,109,940 B1
(45) Date of Patent: Sep. 7, 2021

(54) DEVICES, APPARATUSES, SYSTEMS AND METHODS FOR FACILITATING CLEANING OF AN IMAGING ELEMENT OF AN IMAGING DEVICE

(71) Applicant: ClearCam Inc., Austin, TX (US)

(72) Inventors: Alexander Ross Cohen, Austin, TX (US); Christopher Robert Idelson, Austin, TX (US); Mitchell Ross Gilkey, Austin, TX (US)

(73) Assignee: ClearCam Inc., Austin, TX (US)

( * ) Notice: Subject to any disclaimer, the term of this patent is extended or adjusted under 35 U.S.C. 154(b) by 0 days.

(21) Appl. No.: 17/171,568

(22) Filed: Feb. 9, 2021

(51) Int. Cl.
*A61B 90/70* (2016.01)
*A61B 34/30* (2016.01)

(52) U.S. Cl.
CPC .............. *A61B 90/70* (2016.02); *A61B 34/30* (2016.02)

(58) Field of Classification Search
CPC ................................. A61B 90/70; A61B 34/30
See application file for complete search history.

(56) References Cited

U.S. PATENT DOCUMENTS

| | | | |
|---|---|---|---|
| 5,392,766 | A | 2/1995 | Masterson et al. |
| 5,518,502 | A | 5/1996 | Kaplan et al. |
| 6,451,027 | B1 * | 9/2002 | Cooper .............. A61B 1/00149 606/130 |
| 6,755,782 | B2 | 6/2004 | Ogawa |
| 6,923,759 | B2 | 8/2005 | Kasahara et al. |
| 7,543,314 | B2 | 6/2009 | Kadykowski |
| 7,959,561 | B2 * | 6/2011 | Akui .................. A61B 1/00087 600/157 |
| 8,690,764 | B2 | 4/2014 | Clark et al. |
| 8,979,738 | B2 | 3/2015 | Hsu et al. |
| 9,050,036 | B2 | 6/2015 | Poll et al. |

(Continued)

FOREIGN PATENT DOCUMENTS

| | | |
|---|---|---|
| CN | 101883531 B | 7/2014 |
| EP | 0647425 A1 | 4/1995 |

(Continued)

OTHER PUBLICATIONS

International Search Authority, Notification of Transmittal of the International Search Report and Written Opinion of the International Search Authority, PCT/US2019/063369, 16 pages.

*Primary Examiner* — Richard G Louis
(74) *Attorney, Agent, or Firm* — David O. Simmons; IVC Patent Agency

(57) ABSTRACT

Embodiments of the disclosures made herein are directed to devices, apparatuses, systems and methods for facilitating cleaning of an imaging element of imaging devices used with robotic systems. Devices, apparatuses, systems and methods in accordance with the disclosures made herein provide a lens cleaning device configured to perform one or more cleaning events to remove contaminating matter from an imaging element (e.g., lens) of an imaging device (e.g., a laparoscope). In preferred embodiments, such devices, apparatuses, systems and methods are adapted specifically for facilitating in-vivo cleaning of an imaging element of imaging devices that are used with robotic surgical systems. Advantageously, embodiments of such robotic surgical system implementations enable a surgeon to readily resolve sub-optimal visualization of the surgical field during robotic (e.g., laparoscopic) surgical procedures.

27 Claims, 4 Drawing Sheets

(56) References Cited

U.S. PATENT DOCUMENTS

| | | |
|---|---|---|
| 9,486,129 B2 | 11/2016 | Rodriguez Sanjuan |
| 9,763,567 B2 | 9/2017 | O'Prey et al. |
| 10,791,918 B1 | 10/2020 | Gilkey et al. |
| 2003/0139649 A1* | 7/2003 | Kasahara ........... A61B 1/00087 600/157 |
| 2009/0229067 A1 | 9/2009 | Becker et al. |
| 2009/0250081 A1 | 10/2009 | Gordin et al. |
| 2012/0101338 A1 | 4/2012 | O'Prey et al. |
| 2014/0094650 A1 | 4/2014 | Schaning |
| 2016/0128551 A1 | 5/2016 | Hsu et al. |
| 2017/0332893 A1 | 11/2017 | Irion et al. |
| 2017/0367571 A1 | 12/2017 | Nave |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2015031026 A | 2/2015 |
| JP | 5735908 B2 | 6/2015 |
| WO | 200912587 A2 | 10/2009 |
| WO | 2014034839 A1 | 3/2014 |
| WO | WO2017006684 | 12/2017 |
| WO | 2020112852 A1 | 4/2020 |

\* cited by examiner

DEVICES, APPARATUSES, SYSTEMS AND METHODS FOR FACILITATING CLEANING OF AN IMAGING ELEMENT OF AN IMAGING DEVICE

FIELD OF THE DISCLOSURE

The disclosures made herein relate generally to lens cleaning devices, apparatuses and methodologies and, more particularly, to devices, apparatuses, systems and methods for facilitating cleaning of an imaging element of an imaging device.

BACKGROUND

There are many types of operational procedures that require visualization of structures located within an enclosed cavity of a body of material (i.e., a body cavity). Such operational procedures are known to use an imaging device having a portion thereof that is insertable into the body cavity for acquiring imaging information of structures within the body cavity. Robotic and manual laparoscopic surgery (i.e., closed or minimally-invasive surgery) are two types of surgical procedures that require visualization of body structures located within a body cavity of a patient.

It is well known in the art that surgeons performing surgical procedures using a visualization scope (e.g., a laparoscope) are often required to operate with a sub-optimal (i.e., an obscured) field of view when visualization of such surgical field becomes sub-optimal. Such a sub-optimal field of view arises from bodily materials (e.g., fat, tissue, blood, moisture and the like) collecting or being deposited on an imaging element (e.g., lens) of a scope (e.g., laparoscope) used to provide in-vivo visualization while performing surgical procedures using a laparoscope or the like. One reason for visualization of the surgical field becoming sub-optimal during laparoscopic surgery arises from gradual contamination of the imaging element leading to the delayed recognition that the visualization of the surgical field has become diminished to the point where cleaning of the imaging element is required or desired. Another reason for visualization of the surgical field becoming sub-optimal during laparoscopic surgery arises from a surgeon intentionally delaying cleaning of the imaging element to preclude interruption of the surgical procedure, particularly when cleaning is performed outside of the body cavity—i.e., ex-vivo.

Typically, when a surgeon's visualization of the surgical field becomes sub-optimal during laparoscopic surgery, an imaging element of the imaging device must be cleaned. To date, the most prevalent approaches for cleaning contaminants from the surface of the imaging element are performed ex-vivo after removing the imaging element of the laparoscope from the surgical field. These ex-vivo cleaning approaches are known to often be less than desirable, as they are inefficient, frustrating, and can introduce adverse considerations relative to patient safety and medical outcomes. In some instances, a surgeon may attempt to wipe the imaging element on nearby body tissue for attempting to remove contaminants. However, such approach is known to provide marginal results and may lead to further contamination of the imaging element.

Various approaches (e.g., devices and techniques) for in-vivo cleaning of the imaging element are known. One such approach comprises the use of pneumatic or liquid irrigation to remove contaminants from the imaging element. Another such approach comprises the use of mechanical wiping methods, such as via a wiper, absorbent pad or the like. Still another such approach comprises use of a polymeric film than can be translated over the imaging element, thereby allowing a contaminated segment of the film to be selectively replaced by a clean (e.g., new) segment of the film. However, development of these in-vivo cleaning approaches has been limited to laparoscopes used in non-robotic surgical implementations.

Therefore, devices, apparatuses, systems and methods for facilitating cleaning of an imaging element of imaging devices that are used with robotic systems would be advantageous, desirable and useful.

SUMMARY OF THE DISCLOSURE

Embodiments of the disclosures made herein are directed to devices, apparatuses, systems and methods for facilitating cleaning of an imaging element of imaging devices used with robotic systems. Such devices, apparatuses, systems and methods in accordance with the disclosures made herein provide a lens cleaning device configured to perform one or more cleaning events to remove contaminating matter from an imaging element (e.g., lens) of an imaging device (e.g., a laparoscope). In preferred embodiments, such devices, apparatuses, systems and methods are adapted specifically for facilitating in-vivo cleaning of an imaging element of imaging devices that are used with robotic surgical systems. Advantageously, embodiments of such robotic surgical system implementations enable a surgeon to readily resolve sub-optimal visualization of the surgical field during robotic (e.g., laparoscopic) surgical procedures while the imaging element remains in-vivo.

In one or more embodiments of the disclosures made herein, an imaging element cleaning apparatus comprises a surgical system attachment body, a sheath assembly, a sheath mount and a motion control device. The surgical system attachment body is adapted for being engaged with one or more structural components of a robotic surgical system for at least partially securing the imaging element cleaning apparatus thereto. The sheath assembly comprises a scope sheath, a cleaning member and a coupling element. The coupling element is movably attached to the scope sheath. The cleaning member is attached to a first end portion of the coupling element and is adjacent a first end portion of the scope sheath. The sheath mount is attached to the surgical system attachment body. The scope sheath is attached at a second end portion thereof to the sheath mount. The motion control device has a mounting portion attached to the surgical system attachment body and a rotational movement imparting portion attached to a second end portion of the coupling element.

In another embodiment of the disclosures made herein, an imaging element cleaning apparatus comprises a chassis, at least one surgical system attachment body, a sheath assembly and a drive unit. The at least one surgical system attachment body is coupled to the chassis. The at least one surgical system attachment body is adapted for being engaged with one or more structural components of a robotic surgical system for at least partially securing the imaging element cleaning apparatus thereto. The sheath assembly comprises a scope sheath, a cleaning member and a coupling element. The coupling element is movably attached to the scope sheath. The cleaning member is fixedly attached to a first end portion of the coupling element and is adjacent a first end portion of the scope sheath. The drive unit is coupled to the chassis. The drive unit comprises at least one movement actuator and a sheath mount. The scope sheath is attached at a second end portion thereof to the sheath mount. The at least one movement actuator is attached to a second end portion of the coupling element for enabling the coupling element to be selectively rotated thereby and to be selectively translated axially thereby.

In another embodiment of the disclosures made herein, a method of facilitating cleaning of an imaging element of a visualization scope of a robotic surgical system comprises a plurality of steps. A step is performed to provide a drive unit comprising a surgical system attachment body, a sheath mount attached to the surgical system attachment body and a motion control device having a mounting portion thereof attached to the surgical system attachment body. The surgical system attachment body is adapted to be engaged with one or more structural components of the robotic surgical system. A step is performed to provide a sheath assembly comprising a scope sheath, a cleaning member and a coupling element. The coupling element is movably attached to the scope sheath and wherein the cleaning member is attached to a first end portion of the coupling element and is adjacent a first end portion of the scope sheath. A step is performed to attach a second end portion of the scope sheath to the sheath mount. A step is performed to attach a second end portion of the coupling element to a rotational movement imparting portion of the motion control device. A step is performed to engage the surgical system attachment body with one or more structural components of the robotic surgical system.

In one or more embodiments, the scope sheath is detachably attached to the sheath mount.

In one or more embodiments, the scope sheath is fixedly attached to the sheath mount.

In one or more embodiments, the sheath assembly further comprises a sheath mounting body attached to the second end portion of the scope sheath and the sheath mounting body is detachably attached to the sheath mount.

In one or more embodiments, the coupling element further comprises an engagement body attached to the second end portion thereof and the engagement body is detachably attached to the rotational movement imparting portion of the motion control device.

In one or more embodiments, the motion control device comprises a first movement actuator adapted to provide rotational movement of a structure attached to a motion imparting portion thereof and a second movement actuator adapted to provide axial movement of a structure attached to a motion imparting portion thereof, the coupling element is attached to the motion imparting portion of the first movement actuator and a mounting portion of the first movement actuator is attached to the motion imparting portion of the second actuation device.

In one or more embodiments, the motion control device comprises a rotational motion imparting portion and an axial motion imparting portion, the coupling element is attached to the rotational motion imparting portion and the coupling element is coupled to the axial motion imparting portion through the rotational motion imparting portion.

In one or more embodiments, the motion control device comprises a first portion thereof attached to the surgical system attachment body and a second portion thereof attached to the coupling element.

In one or more embodiments, the surgical system attachment body further comprises a third portion coupling the first portion to the second portion, the third portion imparts axial movement with respect to the first portion, the second portion imparts rotational movement relative to the first portion and attachment of the first portion to the surgical system attachment body inhibits unrestricted rotational movement and axial movement therebetween.

In one or more embodiments, the surgical system attachment body comprises a scope attachment body adapted to be secured to a structural component of a visualization scope of the robotic surgical system.

In one or more embodiments, the scope attachment body includes a securement portion adapted for engaging an extension portion of the visualization scope.

In one or more embodiments, the securement portion of the scope attachment body has a central passage adapted for having the extension portion of the visualization scope disposed therein and the central passage of the securement portion has a centerline longitudinal axis that extends colinearly with a centerline longitudinal axis of the scope sheath.

These and other objects, embodiments, advantages and/or distinctions of the present invention will become readily apparent upon further review of the following specification, associated drawings and appended claims.

DETAILED DESCRIPTION

Figure 1:
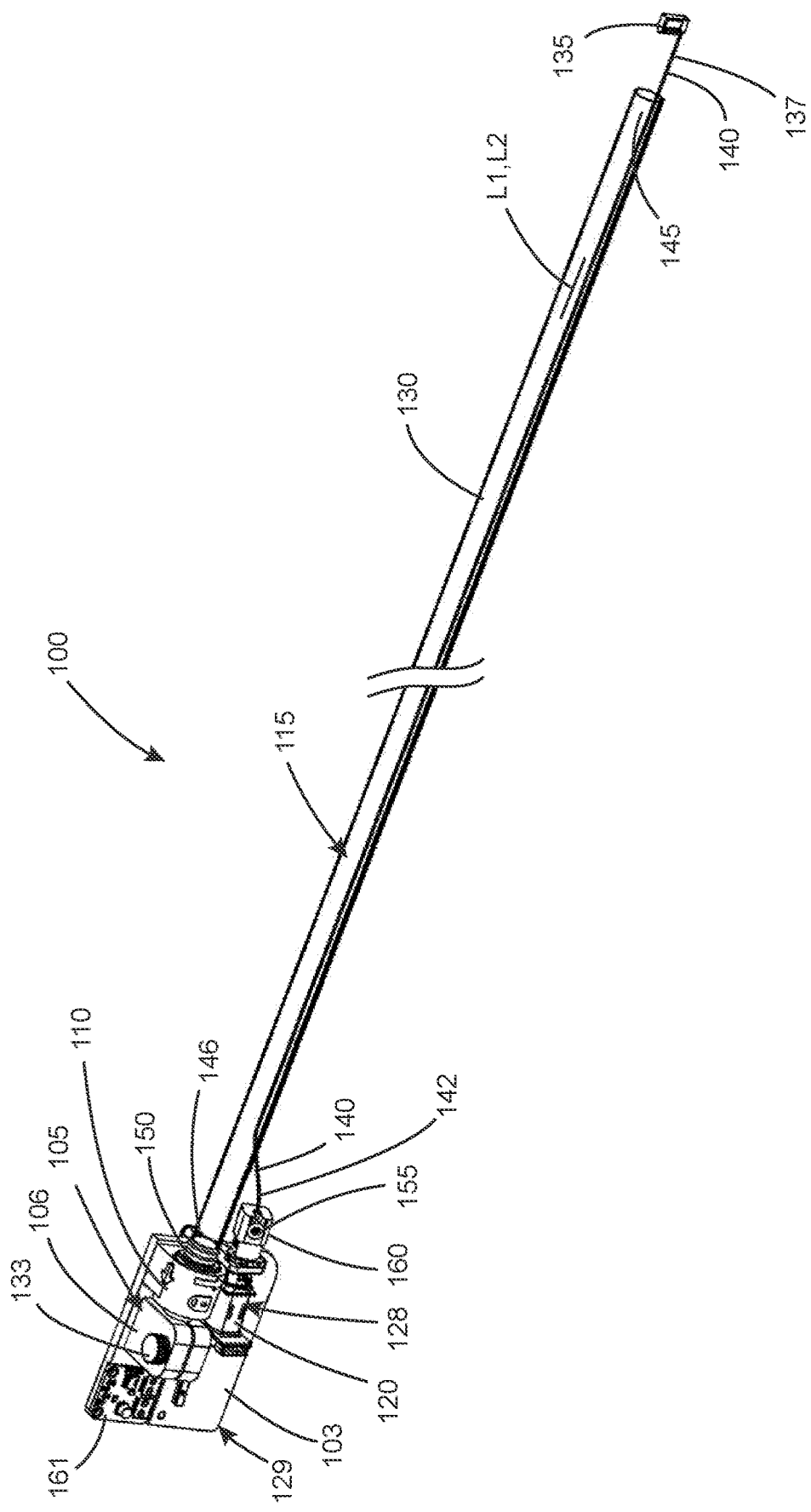
FIG. 1 is a first perspective view showing an imaging element cleaning apparatus in accordance with one or more embodiment of the disclosures made herein.

Referring to FIGS. 1-7, an imaging element cleaning apparatus configured in accordance with one or more embodiments of the disclosures made herein (i.e., the imaging element cleaning apparatus 100) is shown. The imaging element cleaning apparatus 100 includes a chassis 103, a surgical system attachment body 105, a sheath mount 110, a sheath assembly 115, a rotational movement actuator 120 (e.g., a motor) and an axial movement actuator 125 (e.g., a motor). The rotational movement actuator 120 and the axial movement actuator 125 jointly define a motion control device 128. The chassis 103, the surgical system attachment body 105, the sheath mount 110 and the motion control device 128 jointly define a drive unit 129.

Figure 6:
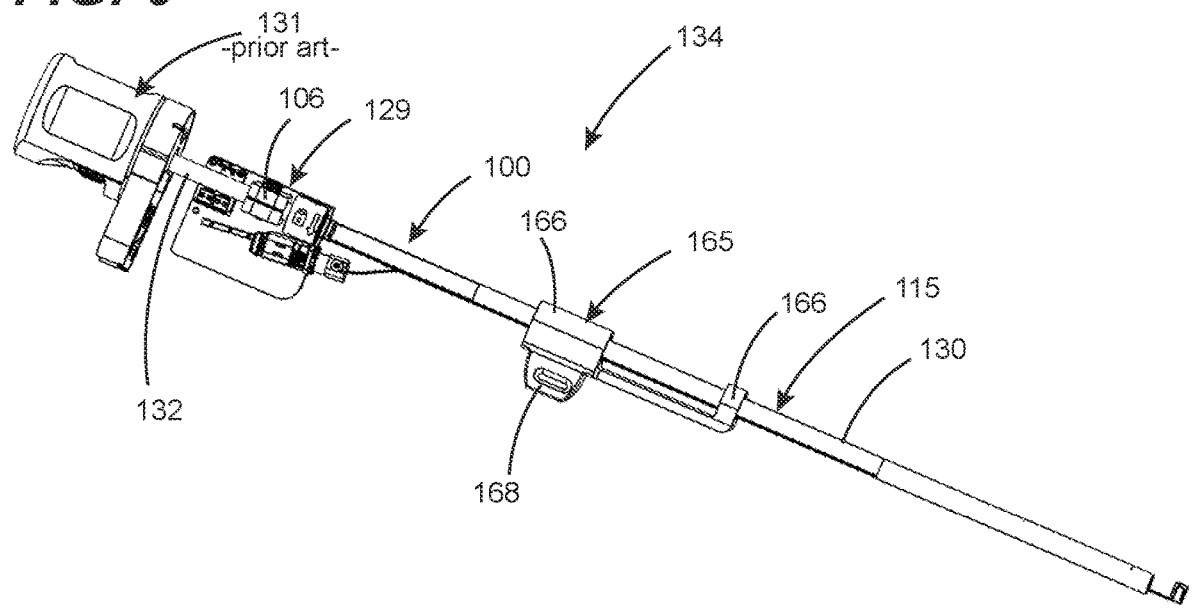
FIG. 6 is a perspective view showing the sheath assembly of the imaging element cleaning apparatus of FIG. 1 and a robotic arm connector in accordance with one or more embodiments of the disclosures made herein attached to a prior art visualization scope.

The surgical system attachment body 105 is adapted for being engaged with one or more structural components of a robotic surgical system for at least partially securing the imaging element cleaning apparatus 100 thereto. A visualization scope 131, as shown in FIG. 6, is one example of such a structural component of a robotic surgical system. In one or more embodiments, as shown, the surgical system attachment body 105 can be (or comprise) a scope attachment body 106 adapted to be secured to a structural component of the visualization scope 131. More specifically, in one or more embodiments, the scope attachment body 106 includes a central passage 126 (i.e., a securement portion) adapted for having an extension portion 132 of the visualization scope 131 disposed therein.

Examples of robotic surgical systems include, but are not limited to, those available from Intuitive Surgical, Zimmer Biomet, Medtronic, Stryker, Siemens Healthineers, Johnson & Johnson, and Auris Health. Although disclosed in the context of robotic surgical system, imaging element cleaning apparatus configured in accordance with one or more embodiments of the disclosures made herein may be implemented in a manner adapted for manual laparoscopic imaging devices and surgical methodologies. Examples of commercially available manual laparoscopic imaging devices include, but are not limited to, endoscopes manufactured under brand names of Karl Storz, Linvatec, Olympus, Richard Wolf, Stryker and the like.

The sheath assembly 115 comprises a scope sheath 130, a cleaning member 135 and a coupling element 140. The coupling element 140 is movably attached to the scope sheath 130. For example, the coupling element 140 (i.e., a control wire) can extend through a passage of the scope sheath such as an open or closed channel, groove, or the like. The cleaning member 135 is attached to a first end portion 137 of the coupling element 140 and is adjacent a first end portion 145 of the scope sheath 130. The scope sheath 130 may be detachably or fixedly attached to the sheath mount 110. The central passage 126 preferably has a centerline longitudinal axis L1 that extends colinearly with a centerline longitudinal axis L2 of the scope sheath 130.

The scope sheath 130 may be a thin-walled tube made from a metallic, composite and/or polymeric material. The coupling element 140 may be a flexible small-diameter wire, cable, tubular structure or the like made from a metallic, fibrous, polymeric material and/or the like. In some embodiments, the coupling element 140 is characterized by an elongated small diameter structure that offers at least a limited degree of bendability in combination with high torsional rigidity. In other embodiments, the coupling element 140 is characterized by an elongated small diameter structure that offers a given (e.g., predictable) amount of torsional compliance. Based on these characterizing attributes, examples of coupling element 140 include, but are not limited to, solid metallic wire, tube, spiraled metal wire, a polymeric filament(s), a composite filament(s) or the like. In one or more embodiments, the coupling member 140 may be used to deliver a flowable material (e.g., gas or liquid material) to the first end portion 137 of the scope sheath 130.

As shown, the sheath assembly 115 (i.e., a "cleaning cartridge") docks to the drive unit 129 at two locations. The sheath assembly 115 comprises a sheath mounting body 150 attached to a second end portion 146 of the scope sheath 130. The sheath mounting body 150 is detachably attached to the sheath mount 110 such as by pins 151 (i.e., protrusions) that each engage a mating groove (i.e., a mating features for providing an interlocked interface). Such mating features may be configured for defining/providing a desired angular "clocking" of the sheath assembly 115 relative to the drive unit 129. The interlocked interface either alone or in combination with a supplemental interlocking structure (e.g., a spring-loading structure) may be configured to secure the scope sheath 130 in a positionally and rotationally locked configuration relative to the sheath mount 110. The sheath assembly 115 also comprises a coupling element engagement body 155 attached to a second end portion 142 of the coupling element 140 such as via a fastener that secures the coupling element at a fixed location along a length of the coupling element 140. The coupling element engagement body 155 is located on the coupling element 140 at a prescribed distance from the cleaning member 135. As shown, the coupling element engagement body 155 may be embodied as a tapered body. The coupling element engagement body 155 may be selectively and securely engageable with a mating engagement body 160 of the rotational movement actuator 120. These engagement arrangements of the scope sheath 130 and the coupling element 140 individually and jointly provide for a simple, yet effective and efficient approach for mechanically securing the sheath assembly 115 to the drive unit 129 such as to enable selective interchangeability/replacement of sheath assemblies (e.g., 0-degree wiper sheath assembly or 30-degree wiper sheath assembly).

As shown in FIG. 6, in one or more embodiments of the disclosures made herein, the imaging element cleaning apparatus 100 may be securely engaged with the visualization scope 131 via the scope attachment body 106 (i.e., a surgical system attachment body), thereby forming a cleaning device enabled visualization scope 134. To this end, the extension portion 132 of the visualization scope 131 extends through the central passage 126 of the scope attachment body 106. The scope attachment body 106 may be in the form of a clamp whereby a securement fastener 133 is used to exert a clamping for on the extension portion 132 by the scope attachment body 106, thereby fixedly securing the drive unit 129 to the visualization scope 134. In view of the disclosures made herein, a skilled person will recognize other approaches for securing the drive unit 129 to the visualization scope 131.

Figure 7:
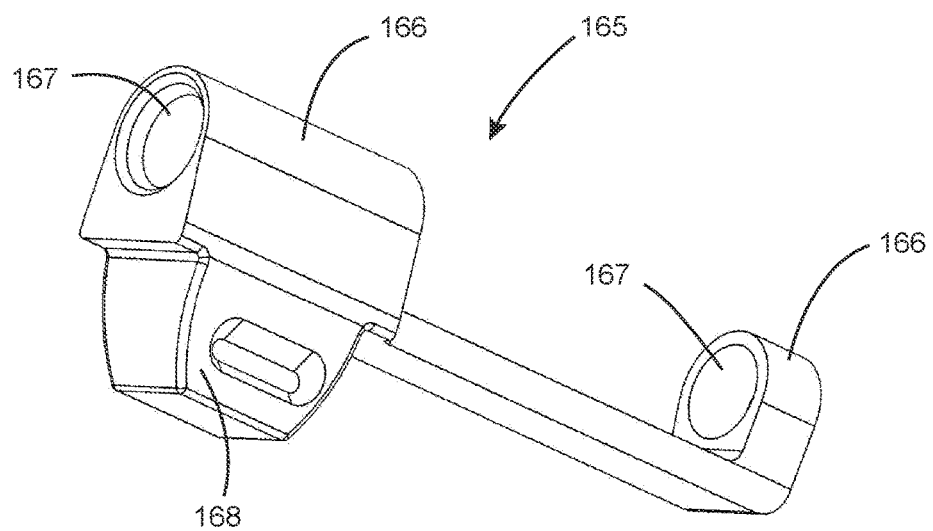
FIG. 7 is a perspective view showing a robotic arm connector in accordance with one or more embodiment of the disclosures made herein.

A robotic arm mount of a robotic surgical system is another example of a structural components of a robotic surgical system through which an imaging element cleaning apparatus in accordance with one or more embodiments of the disclosures made herein may be at least partially secured thereto. As shown in FIGS. 6 and 7, a robotic arm connector 165 may be moveably attached to the scope sheath 130 to provide for connection with a robotic arm mount such as by the scope sheath 130 passing through a central passages 166 of the robotic arm connector 165. Typically, connection of an imaging element cleaning apparatus configured in accordance with one or more embodiments of the disclosures made herein via the robotic arm connector 165 is used in combination with one or more other robotic arm connections located remotely from the robotic arm connector 165. Spacing between the robotic arm connections serves to provide for stability and rigidity of the as-mounted imaging element cleaning apparatus.

Referring to FIGS. 6 and 7, the robotic arm connector 165 may be configured to mimic the structural support provided for by a cannula typically mounted on a robotic arm and through which a surgical instrument (e.g., a visualization scope) passes. As is well known, a length of the cannula serves to provide an elongated bearing-surface upon which an extension portion of the surgical instrument (e.g., the extension portion 132 of the visualization scope 131) bears and slides and to provide support against loadings resulting from forces generated by pivoting of the surgical instrument while the surgical instrument extends through a patient's abdominal wall. To this end, the robotic arm connector 165 may be configured in a similar manner with spaced apart and/or elongated support portions 166 that each carry a respective and linearly aligned central passage 167. The robotic arm connector 165 includes an arm engaging portion 168 configured for being engaged by a mating engagement portion of an arm of a robotic surgical system.

Figure 2:
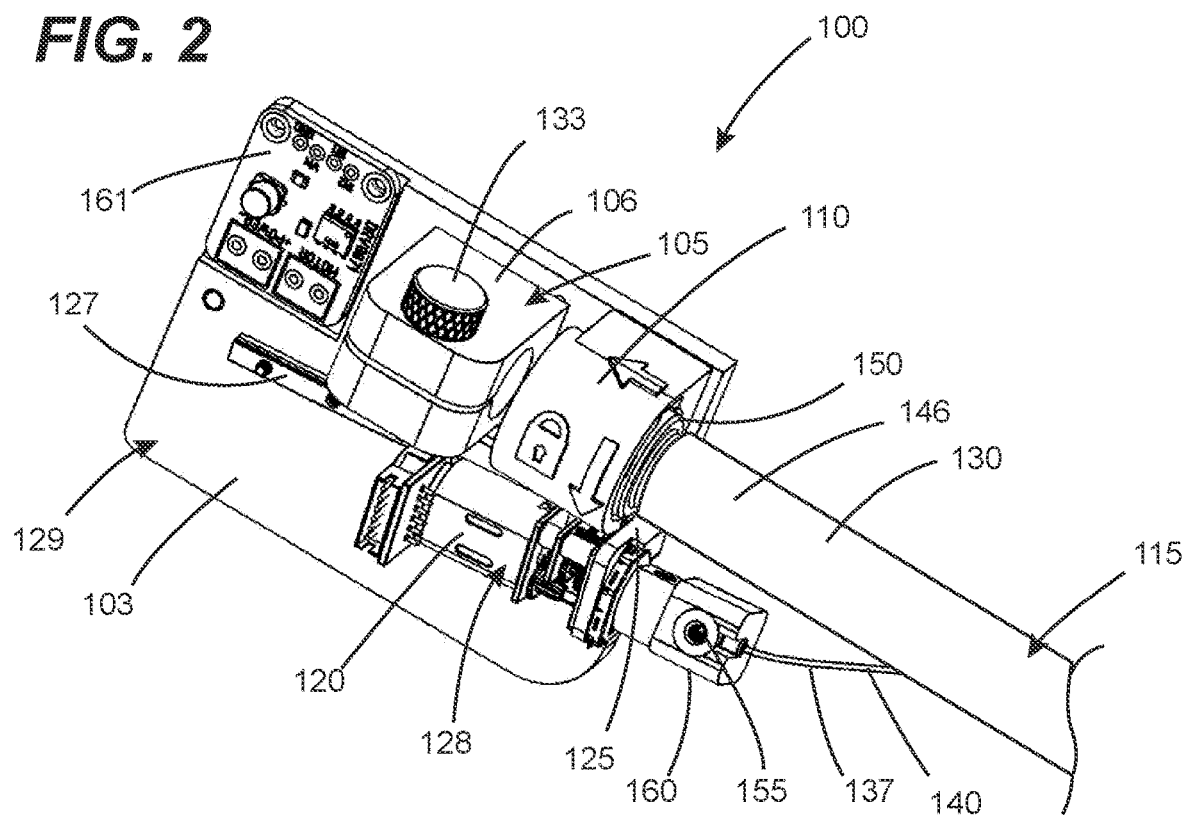
FIG. 2 is a second perspective view showing a respective portion of the imaging element cleaning apparatus of FIG. 1.
Figure 3:
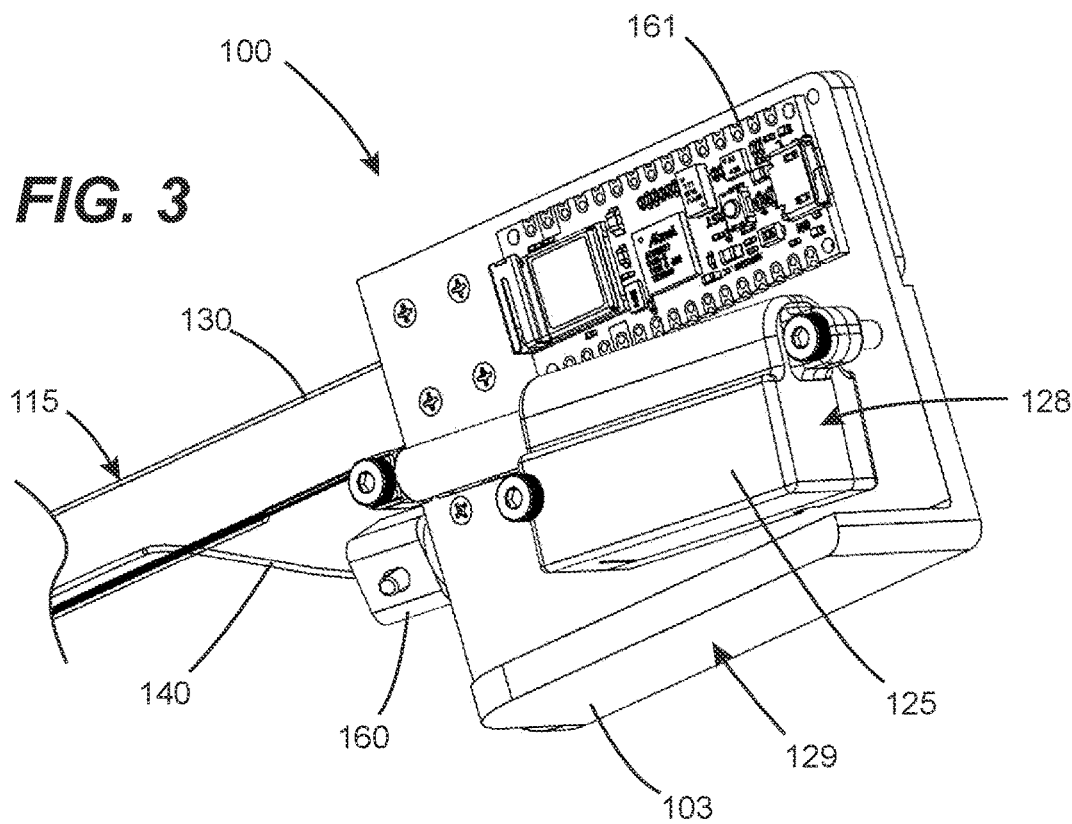
FIG. 3 is a third perspective view showing a respective portion of the imaging element cleaning apparatus of FIG. 1.
Figure 4:
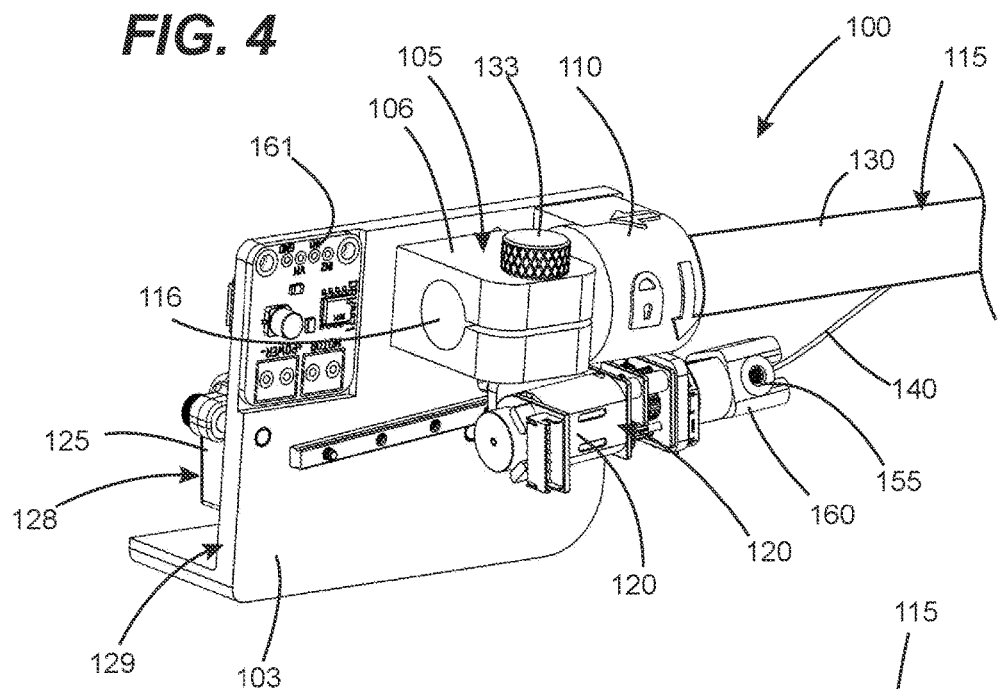
FIG. 4 is a partial perspective view showing a respective portion of the imaging element cleaning apparatus of FIG. 1.
Figure 5B:
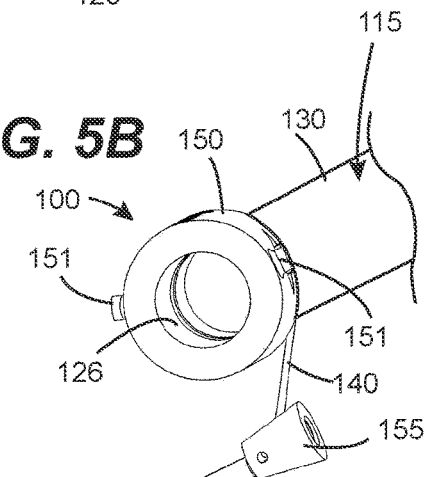
FIG. 5B is an enlarge fragmentary view of a second end portion of the sheath assembly of FIG. 5A.
Figure 5A:
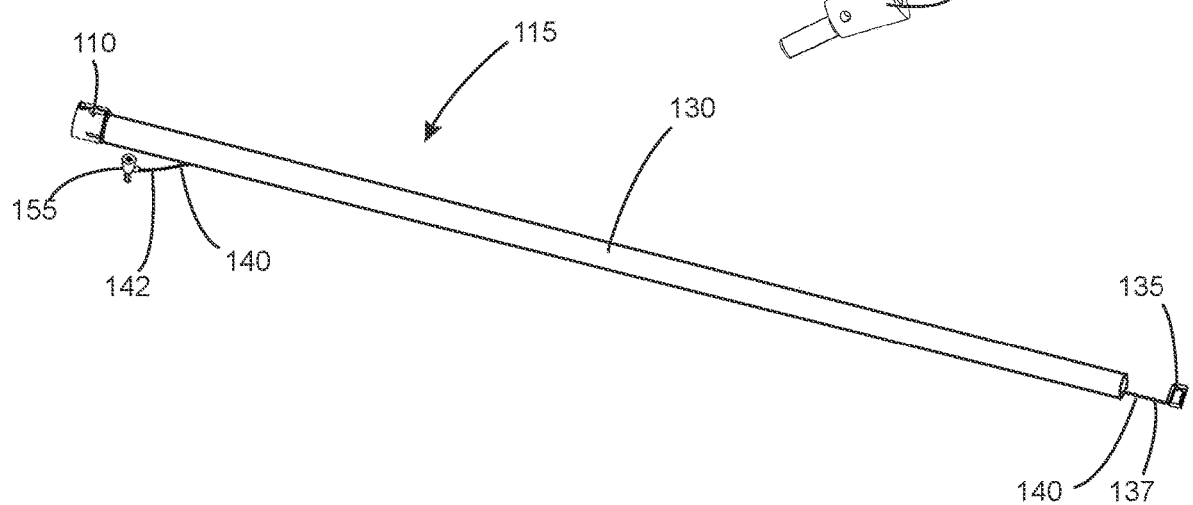
FIG. 5A is a perspective view showing an embodiment of a sheath assembly in accordance with one or more embodiments of the disclosures made herein.

As related to the motion control device 128 best shown in FIGS. 1 and 2, the rotational movement actuator 120 is a rotational movement imparting portion thereof and the axial movement actuator 125 is an axial movement imparting portion thereof. Thus, a person of ordinary skill will appreciate that the rotational movement actuator 120 is a first movement actuator adapted to provide rotational movement of a structure coupled to a motion imparting portion thereof and the axial movement actuator 125 is a second movement actuator adapted to provide axial movement of a structure coupled to (e.g., directly attached to) a motion imparting portion thereof. In one or more embodiments, as shown, a mounting portion of the axial movement actuator 125 is attached to the chassis 103 or the surgical system attachment body 105, a mounting portion of the rotational movement actuator 120 is attached to an axial movement imparting portion of the axial movement actuator 125 and the coupling element 140 is attached to a rotational movement imparting portion of the rotational movement actuator 120. The rotational movement actuator 120 can be attached to the chassis 103 or the surgical system attachment body 105 for limiting translational movement of the entire rotational movement actuator 120 to being along a particular axial translation axis—e.g., via a motion control device 127 (e.g., a slide rail) that limits movement to being along an axial translation axis thereof. This arrangement of the motion control device 128 enables independent rotational movement and axial movement of the cleaning member 135 relative to the first end portion 145 of the scope sheath 130 via selective actuation of the rotational movement actuator 120 and the axial movement actuator 125. It is contemplated and disclosed herein that, in one or more other embodiments, such independent rotational movement and axial movement of the cleaning member 135 may be provided via a single movement actuator or more than two movement actuators. It is also contemplated and disclosed herein that, in one or more other embodiments, such single movement actuator or more than two movement actuators may each be an actuator (e.g., motor) integral with a structural component of a robotic surgical system—e.g., motors integral with a robotic arm of a robotic surgical system controlled by a control apparatus of the robotic surgical system.

In one or more embodiments, as shown, operation of the motion control device 128 (e.g., the rotational movement actuator 120 and the axial movement actuator 125) may be controlled via a movement controller 161—e.g., one or more micro-controllers comprising basic programmable control logic instructions/code/software). For example, in response to the movement controller 161 receiving a cleaning event trigger signal (e.g., via a manual actuation button or system-issued signal), the movement controller 161 issues one or more corresponding signals for causing the motion control device 128 to correspondingly move the cleaning member rotationally and, optionally, axially.

Disclosed now is a method of facilitating cleaning of an imaging element of a visualization scope of a robotic surgical system in accordance with one or more embodiments of the disclosures made herein. The objective of such a method includes arriving at an imaging element cleaning apparatus configured in accordance with one or more embodiments of the disclosures made herein (e.g., as discussed above in reference to FIGS. 1-7), arriving at a cleaning device enabled visualization scope (e.g., as discussed above in reference to FIGS. 4 and 6) or the like. Following are examples of steps that may be taken for performing such a method of facilitating cleaning of an imaging element of a visualization scope of a robotic surgical system, in the order described or otherwise. A step may be performed to provide a drive unit, such as that discussed above, where the drive unit comprising one or more surgical system attachment bodies, a sheath mount attached to at least one of the surgical system attachment bodies and a motion control device having a mounting portion thereof attached to the surgical system attachment body and where the surgical system attachment body is adapted to be engaged with one or more structural components of the robotic surgical system. A step may be performed to provide a sheath assembly, such as that discussed above, where the sheath assembly comprises a scope sheath, a cleaning member and a coupling element, where the coupling element is movably attached to the scope sheath and where the cleaning member is attached to a first end portion of the coupling element and is adjacent a first end portion of the scope sheath. A step may be performed to attach a second end portion of the scope sheath to the sheath mount. A step may be performed to attach a second end portion of the coupling element to a rotational movement imparting portion of the motion control device. A step may be performed to engage at least one of the surgical system attachment bodies with one or more structural components of the robotic surgical system.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An imaging element cleaning apparatus, comprising:
    a surgical system attachment body adapted for being engaged with one or more structural components of a robotic surgical system for at least partially securing the imaging element cleaning apparatus thereto;
    a sheath assembly comprising a scope sheath, a cleaning member and a coupling element, wherein the coupling element is movably attached to the scope sheath and wherein the cleaning member is attached to a first end portion of the coupling element and is adjacent a first end portion of the scope sheath;
    a sheath mount attached to the surgical system attachment body, wherein the scope sheath is attached at a second end portion thereof to the sheath mount; and
    a motion control device having a mounting portion attached to the surgical system attachment body and a rotational movement imparting portion attached to a second end portion of the coupling element;
    wherein the scope sheath is detachably attached to the sheath mount.

2. The imaging element cleaning apparatus of claim 1 wherein the scope sheath is fixedly attached to the sheath mount.

3. The imaging element cleaning apparatus of claim 1 wherein:

the sheath assembly further comprises a sheath mounting body attached to the second end portion of the scope sheath; and the sheath mounting body is detachably attached to the sheath mount.

4. An imaging element cleaning apparatus, comprising:
a surgical system attachment body adapted for being engaged with one or more structural components of a robotic surgical system for at least partially securing the imaging element cleaning apparatus thereto;
a sheath assembly comprising a scope sheath, a cleaning member and a coupling element, wherein the coupling element is movably attached to the scope sheath and wherein the cleaning member is attached to a first end portion of the coupling element and is adjacent a first end portion of the scope sheath;
a sheath mount attached to the surgical system attachment body, wherein the scope sheath is attached at a second end portion thereof to the sheath mount; and
a motion control device having a mounting portion attached to the surgical system attachment body and a rotational movement imparting portion attached to a second end portion of the coupling element;
wherein:
the coupling element further comprises an engagement body attached to the second end portion thereof; and
the engagement body is detachably attached to the rotational movement imparting portion of the motion control device.

5. The imaging element cleaning apparatus of claim 1 wherein:
the motion control device further comprises an axial movement imparting portion coupled to the mounting portion thereof and to the rotational movement imparting portion for enabling axial translation of the rotational movement imparting portion relative to the mounting portion.

6. The imaging element cleaning apparatus of claim 5 wherein said attachment of the mounting portion of the motion control device to the surgical system attachment body inhibits at least axial movement therebetween.

7. The imaging element cleaning apparatus of claim 1 wherein the surgical system attachment body comprises a scope attachment body adapted to be secured to a structural component of a visualization scope of the robotic surgical system.

8. The imaging element cleaning apparatus of claim 7 wherein the scope attachment body includes a securement portion adapted for engaging an extension portion of the visualization scope.

9. The imaging element cleaning apparatus of claim 8 wherein:
the securement portion of the scope attachment body has a central passage adapted for having the extension portion of the visualization scope disposed therein; and
the central passage of the securement portion has a centerline longitudinal axis that extends colinearly with a centerline longitudinal axis of the scope sheath.

10. An imaging element cleaning apparatus, comprising:
a chassis;
at least one surgical system attachment body coupled to the chassis, wherein the at least one surgical system attachment body is adapted for being engaged with one or more structural components of a robotic surgical system for at least partially securing the imaging element cleaning apparatus thereto;
a sheath assembly comprising a scope sheath, a cleaning member and a coupling element, wherein the coupling element is movably attached to the scope sheath and wherein the cleaning member is fixedly attached to a first end portion of the coupling element and is adjacent a first end portion of the scope sheath; and
a drive unit coupled to the chassis, wherein the drive unit comprises at least one movement actuator and a sheath mount, wherein the scope sheath is attached at a second end portion thereof to the sheath mount and wherein the at least one movement actuator is attached to a second end portion of the coupling element for enabling the coupling element to be selectively rotated thereby and to be selectively translated axially thereby;
wherein the scope sheath is detachably attached to the sheath mount.

11. The imaging element cleaning apparatus of claim 10 wherein the scope sheath is fixedly attached to the sheath mount.

12. The imaging element cleaning apparatus of claim 10 wherein:
the sheath assembly further comprises a sheath mounting body attached to the second end portion of the scope sheath; and
the sheath mounting body is detachably attached to the sheath mount.

13. An imaging element cleaning apparatus, comprising:
a chassis;
at least one surgical system attachment body coupled to the chassis, wherein the at least one surgical system attachment body is adapted for being engaged with one or more structural components of a robotic surgical system for at least partially securing the imaging element cleaning apparatus thereto;
a sheath assembly comprising a scope sheath, a cleaning member and a coupling element, wherein the coupling element is movably attached to the scope sheath and wherein the cleaning member is fixedly attached to a first end portion of the coupling element and is adjacent a first end portion of the scope sheath; and
a drive unit coupled to the chassis, wherein the drive unit comprises at least one movement actuator and a sheath mount, wherein the scope sheath is attached at a second end portion thereof to the sheath mount and wherein the at least one movement actuator is attached to a second end portion of the coupling element for enabling the coupling element to be selectively rotated thereby and to be selectively translated axially thereby;
wherein:
the coupling element further comprises an engagement body attached to the second end portion thereof; and
the engagement body is detachably attached to the rotational movement imparting portion of the at least one movement actuator.

14. An imaging element cleaning apparatus, comprising:
a chassis;
at least one surgical system attachment body coupled to the chassis, wherein the at least one surgical system attachment body is adapted for being engaged with one or more structural components of a robotic surgical system for at least partially securing the imaging element cleaning apparatus thereto;
a sheath assembly comprising a scope sheath, a cleaning member and a coupling element, wherein the coupling element is movably attached to the scope sheath and wherein the cleaning member is fixedly attached to a first end portion of the coupling element and is adjacent a first end portion of the scope sheath; and a drive unit coupled to the chassis, wherein the drive unit comprises at least one movement actuator and a sheath mount, wherein the scope sheath is attached at a second end portion thereof to the sheath mount and wherein the at least one movement actuator is attached to a second end portion of the coupling element for enabling the coupling element to be selectively rotated thereby and to be selectively translated axially thereby;

wherein:
the at least one movement actuator comprises a first movement actuator adapted to provide rotational movement of a structure attached to a motion imparting portion thereof and a second movement actuator adapted to provide axial movement of a structure attached to a motion imparting portion thereof;
the coupling element is attached to the motion imparting portion of the first movement actuator; and
a mounting portion of the first movement actuator is attached to the motion imparting portion of the second actuation device.

15. The imaging element cleaning apparatus of claim 10 wherein:
the at least one movement actuator comprises a rotational motion imparting portion and an axial motion imparting portion;
the coupling element is attached to the rotational motion imparting portion; and
the coupling element is coupled to the axial motion imparting portion through the rotational motion imparting portion.

16. The imaging element cleaning apparatus of claim 10 wherein the at least one movement actuator comprises a first portion thereof attached to the surgical system attachment body and a second portion thereof attached to the coupling element.

17. The imaging element cleaning apparatus of claim 16 wherein:
the surgical system attachment body further comprises a third portion coupling the first portion to the second portion;
the third portion imparts axial movement with respect to the first portion;
the second portion imparts rotational movement relative to the first portion; and
said attachment of the first portion to the surgical system attachment body inhibits unrestricted rotational movement and axial movement therebetween.

18. The imaging element cleaning apparatus of claim 10 wherein the surgical system attachment body comprises a scope attachment body adapted to be secured to a structural component of a visualization scope of the robotic surgical system.

19. The imaging element cleaning apparatus of claim 18 wherein the scope attachment body includes a securement portion adapted for engaging an extension portion of the visualization scope.

20. The imaging element cleaning apparatus of claim 19 wherein:
the securement portion of the scope attachment body has a central passage adapted for having the extension portion of the visualization scope disposed therein; and
the central passage of the securement portion has a centerline longitudinal axis that extends colinearly with a centerline longitudinal axis of the scope sheath.

21. A method of facilitating cleaning of an imaging element of a visualization scope of a robotic surgical system, comprising:
providing a drive unit comprising a surgical system attachment body, a sheath mount attached to the surgical system attachment body and a motion control device having a mounting portion thereof attached to the surgical system attachment body, wherein the surgical system attachment body is adapted to be engaged with one or more structural components of the robotic surgical system;
providing a sheath assembly comprising a scope sheath, a cleaning member and a coupling element, wherein the coupling element is movably attached to the scope sheath and wherein the cleaning member is attached to a first end portion of the coupling element and is adjacent a first end portion of the scope sheath;
attaching a second end portion of the scope sheath to the sheath mount;
attaching a second end portion of the coupling element to a rotational movement imparting portion of the motion control device; and
engaging the surgical system attachment body with one or more structural components of the robotic surgical system;
wherein:
the sheath assembly comprises a sheath mounting body attached to the second end portion thereof;
the sheath mounting body and the sheath mount are jointly configured for enabling the sheath mounting body to be selectively engaged and disengaged with the sheath mount;
attaching the second end portion of the scope sheath to the sheath mount includes engaging the sheath mounting body with the sheath mount.

22. The method of claim 21 wherein:
the surgical system attachment body comprises a scope attachment body attached; and
engaging the surgical system attachment body with one or more structural components of the robotic surgical system includes affixing the scope attachment body to a structural component of the visualization scope.

23. A method of facilitating cleaning of an imaging element of a visualization scope of a robotic surgical system, comprising:
providing a drive unit comprising a surgical system attachment body, a sheath mount attached to the surgical system attachment body and a motion control device having a mounting portion thereof attached to the surgical system attachment body, wherein the surgical system attachment body is adapted to be engaged with one or more structural components of the robotic surgical system;
providing a sheath assembly comprising a scope sheath, a cleaning member and a coupling element, wherein the coupling element is movably attached to the scope sheath and wherein the cleaning member is attached to a first end portion of the coupling element and is adjacent a first end portion of the scope sheath;
attaching a second end portion of the scope sheath to the sheath mount;
attaching a second end portion of the coupling element to a rotational movement imparting portion of the motion control device;
engaging the surgical system attachment body with one or more structural components of the robotic surgical system;

providing a robotic arm connector having a central passage adapted to receive an extension portion of the visualization scope;

inserting the extension portion of the visualization scope through the central passage of the robotic arm connector; and engaging the robotic arm connector with a robotic arm of the robotic surgical system.

24. The method of claim 21, further comprising:

inserting an extension portion of the visualization scope into a central passage of the scope sheath prior to engaging the surgical system attachment body with one or more structural components of the robotic surgical system.

25. The method of claim 24 wherein inserting the extension portion of the visualization scope through into the central passage of the scope sheath includes inserting the extension portion of the visualization scope through a central passage of the sheath mount.

26. The method of claim 25 wherein:

the sheath assembly comprises a sheath mounting body attached to the second end portion thereof;

the sheath mounting body and the sheath mount are jointly configured for enabling the sheath mounting body to be selectively engaged and disengaged with the sheath mount;

attaching the second end portion of the scope sheath to the sheath mount includes engaging the sheath mounting body with the sheath mount.

27. The method of claim 26 wherein:

the sheath assembly comprises a sheath mounting body attached to the second end portion thereof;

the sheath mounting body and the sheath mount are jointly configured for enabling the sheath mounting body to be selectively engaged and disengaged with the sheath mount;

attaching the second end portion of the scope sheath to the sheath mount includes engaging the sheath mounting body with the sheath mount.

\* \* \* \* \*